(12) United States Patent
Burgo et al.

(10) Patent No.: US 11,540,991 B2
(45) Date of Patent: Jan. 3, 2023

(54) SELF-NEUTRALIZING AMINO ACID BASED CATIONIC COMPOSITIONS

(71) Applicant: Inolex Investment Corporation, Wilmington, PA (US)

(72) Inventors: Rocco Vincent Burgo, Mullica Hill, NJ (US); Mei Chen, Philadelphia, PA (US); Michael J. Fevola, Belle Mead, NJ (US); Gary Mosser, Tabernacle, NJ (US); Brittany Pease, Philadelphia, PA (US)

(73) Assignee: INOLEX INVESTMENT CORPORATION, Wilmington, DE (US)

( * ) Notice: Subject to any disclaimer, the term of this patent is extended or adjusted under 35 U.S.C. 154(b) by 59 days.

(21) Appl. No.: 16/813,475

(22) Filed: Mar. 9, 2020

(65) Prior Publication Data
US 2020/0281830 A1 Sep. 10, 2020

Related U.S. Application Data

(60) Provisional application No. 62/815,314, filed on Mar. 7, 2019.

(51) Int. Cl.
*A61K 8/44* (2006.01)
*A61K 8/64* (2006.01)
*A61K 8/81* (2006.01)
*A61Q 5/12* (2006.01)

(52) U.S. Cl.
CPC .................. *A61K 8/44* (2013.01); *A61K 8/64* (2013.01); *A61K 8/8141* (2013.01); *A61Q 5/12* (2013.01); *A61K 2800/5426* (2013.01)

(58) Field of Classification Search
None
See application file for complete search history.

(56) References Cited

U.S. PATENT DOCUMENTS

| 6,572,870 | B2 | 6/2003 | Ribier et al. |
| 7,723,387 | B2 | 5/2010 | Smith et al. |
| 8,105,569 | B2 | 1/2012 | Burgo |
| 2018/0369113 | A1 | 12/2018 | Liu et al. |

OTHER PUBLICATIONS

International Search Report, dated May 20, 2020 by the US International Search Authority, Lee Young, Authorized Officer.

*Primary Examiner* — Jessica Worsham
(74) *Attorney, Agent, or Firm* — Cozen O'Connor

(57) ABSTRACT

The invention described herein includes a self-neutralizing amino acid-based cationic composition that contains an amino acid-based cationic ester, a nonionic amphiphile, and an anhydrous buffering agent. In an embodiment, the composition, when dispersed or dissolved in an aqueous solvent, provides a resultant solution/dispersion having a pH of greater than about 4. The amino acid-based cationic ester may be a reaction product of (i) an amino acid having a non-polar side chain, and an amine group that has been neutralized with an acid; with (ii) a long chain fatty alcohol. Also included within the scope of the invention are methods of preparing a self-neutralizing amino acid-based cationic composition, such method including combining an amino acid-based cationic ester, a nonionic amphiphile and an anhydrous buffering agent. The resulting composition is in an anhydrous solid form. Formulations containing the amino acid-based cationic ester and/or a composition that includes it, are also disclosed.

18 Claims, 4 Drawing Sheets

Figure 1. Formulation pH as a function of AABC composition in Examples 4 – 6 and Comparative Examples 4 – 6.

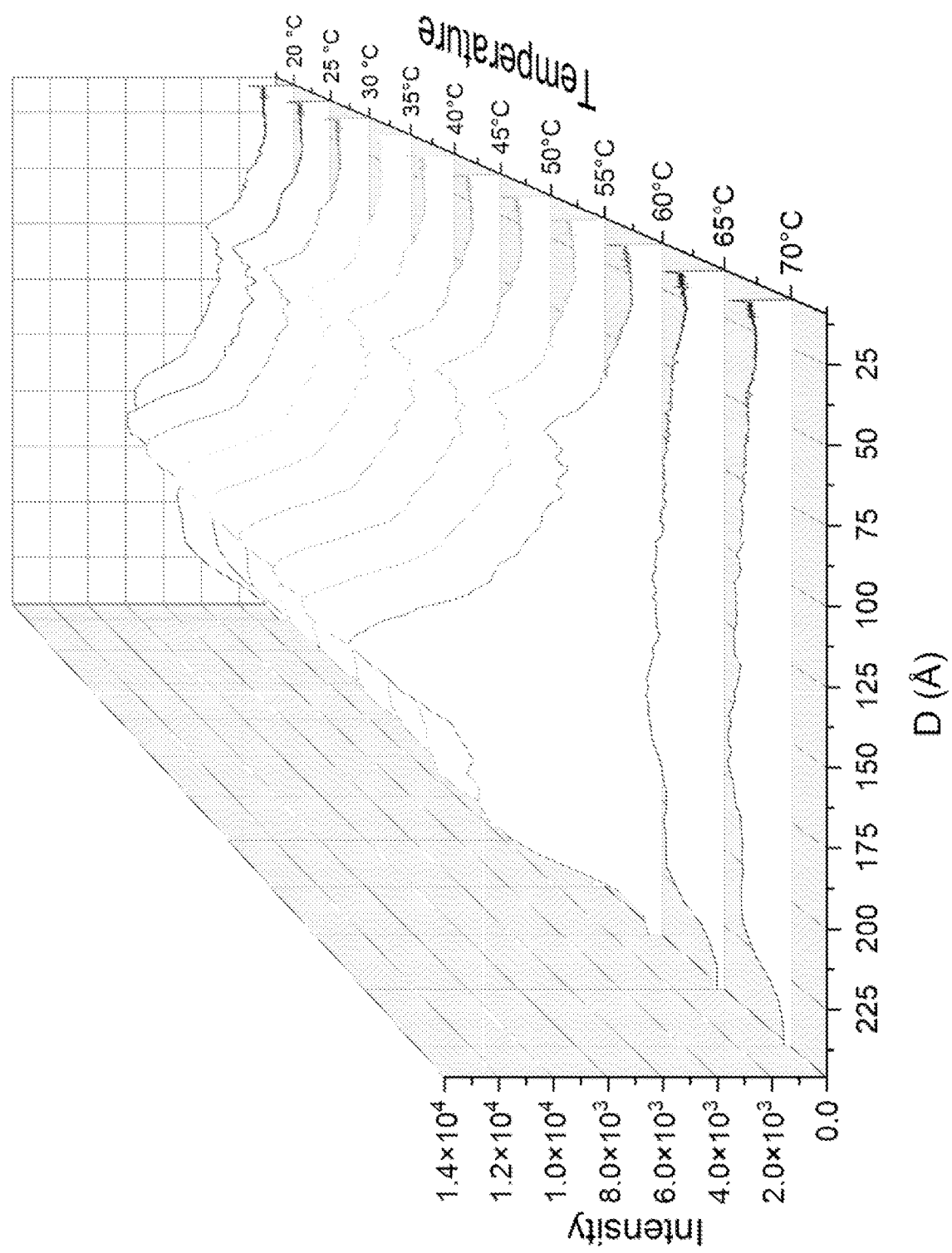
Figure 3. SAXS data for the composition of Example 4 comprising 15% of Example 1 over the temperature range of 20 – 70 °C.

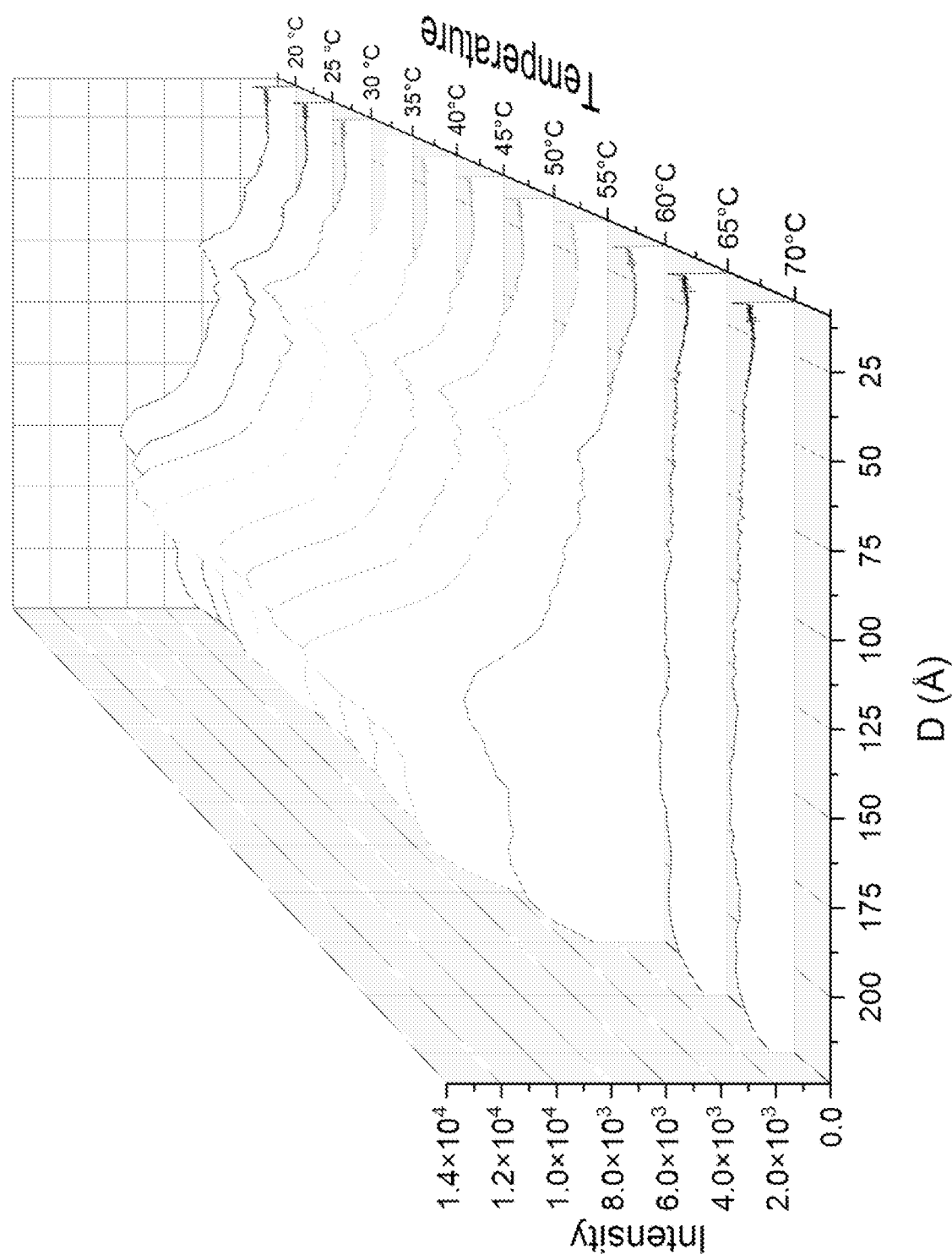
Figure 4. SAXS data for the composition of Example 5 comprising 15% of Example 2 over the temperature range of 20 – 70 °C.

SELF-NEUTRALIZING AMINO ACID BASED CATIONIC COMPOSITIONS

CROSS REFERENCE TO RELATED APPLICATION

This application claims the benefit under 35 U.S.C. § 119(e) of U.S. Provisional Patent Application Ser. No. 62/815,314, filed Mar. 7, 2019, entitled, "Self-Neutralizing Amino-Acid Based Cationic Compositions," the entire disclosure of which is incorporated herein by reference.

BACKGROUND OF THE INVENTION

Non-petrochemically derived cationic emulsifiers that are neutralized amino acid esters are described and claimed in U.S. Pat. No. 8,105,569 of Burgo and its related applications. These amino acid-based cationic esters (hereinafter "AABC"s) of Burgo may be supplied as an anhydrous form, i.e., a form that does not contain water in any significant quantity, e.g., less than about 5% water by weight.

The AABC compositions of Burgo are comprised predominantly of amino acid esters where the amino groups are neutralized by strong organic acids, e.g., ethanesulfonic acid (ESA), which renders the amino acid esters cationically charged species. The AABC compositions may also contain minor quantities, e.g., <2 wt %, of unreacted amino acids, e.g., isoleucine or valine, which are also neutralized by the strong organic acids to yield strongly acidic salts, e.g., isoleucine esylate or valine esylate.

When the AABC compositions of Burgo are dissolved or dispersed in aqueous media, they tend to yield aqueous compositions with rather low pH values, e.g., pH<3.0. Without wishing to be bound by theory, it is believed that these low pH values are attributable to the fact that the AABC is the salt of a strong acid and a weak base. The anion, i.e., the conjugate base of the strong acid, will become a spectator ion and fail to attract protons, while the cation from the weak base will donate protons to the water forming hydronium ions ($H_3O^+$), thus lowering the solution pH value. Additionally, the strongly acidic amino acid salts, e.g., isoleucine esylate or valine esylate, present as unreacted byproducts in the AABC composition, will also contribute to lowering the solution pH.

Such low pH values are undesirable in many applications, especially in personal care and cosmetics, where most products are formulated at pH≥4.0. Previously, formulations prepared with AABCs thus required careful and time-consuming adjustment of pH using suitable bases to achieve stable pH values in the desired range. For example, typical values of skin pH reported in the literature range from pH 4.5-pH 5.0, and this is typically a desired pH value associated with personal care products for topical use on skin. See, e.g., J. W. Weichers, Formulating at pH 4-5: How Lower pH Benefits the Skin and Formulations, *Cosmetics & Toiletries*, 2008, 123(12), 61-70.

There remains a need in the art for an amino acid-based cationic ester that, when included in a formulation, provides a resultant solution/dispersion having a pH suitable for personal care and cosmetic products.

BRIEF SUMMARY OF THE INVENTION

The invention described herein includes a self-neutralizing amino acid-based cationic composition that contains an amino acid-based cationic ester, a nonionic amphiphile, and an anhydrous buffering agent. In an embodiment, the composition, when dispersed or dissolved in an aqueous solvent, provides a resultant solution/dispersion having a pH of greater than about 4.

The amino acid-based cationic ester may be a reaction product of (i) an amino acid having a non-polar side chain, and an amine group that has been neutralized with an acid; with (ii) a long chain fatty alcohol.

Also included within the scope of the invention are methods of preparing a self-neutralizing amino acid-based cationic composition, such method including combining an amino acid-based cationic ester, a nonionic amphiphile and an anhydrous buffering agent. The resulting composition is in an anhydrous solid form.

Formulations containing the amino acid-based cationic ester and/or a composition that includes it, are also disclosed.

BRIEF DESCRIPTION OF THE SEVERAL VIEWS OF THE DRAWING

The foregoing summary, as well as the following detailed description of preferred embodiments of the invention, may be better understood when read in conjunction with the appended drawings.

The invention is not limited to the precise arrangements and instrumentalities shown. In the drawings:

FIG. 3 show SAXS data for lamellar LC systems comprising brassicyl valinate esylate; and FIG. 4 show SAXS data for lamellar LC systems comprising brassicyl isoleucinate esylate.

DETAILED DESCRIPTION OF THE INVENTION

Figure 1:
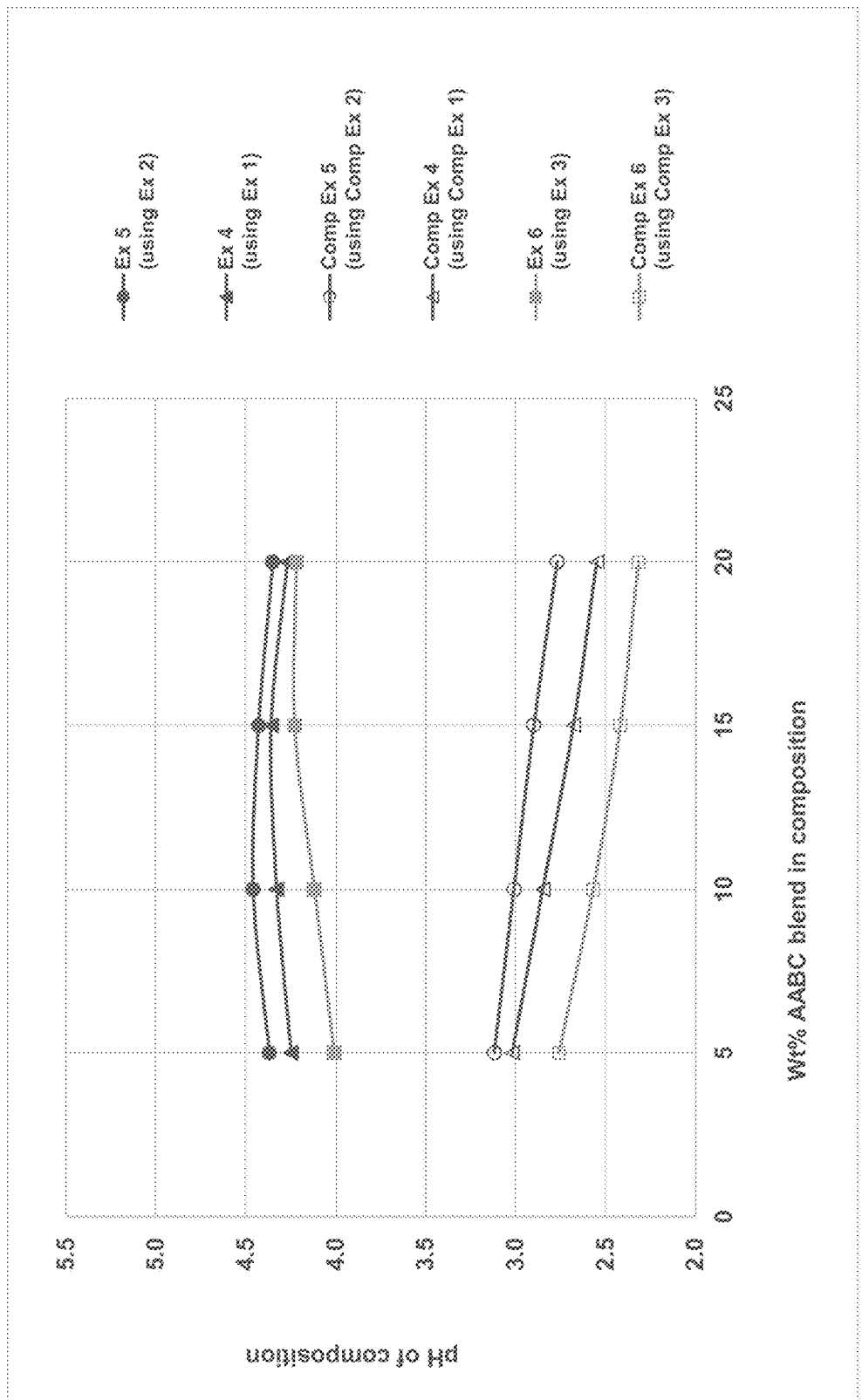
FIG. 1 shows the pH of aqueous compositions as a function of wt % AABC blend in the composition of Examples 4 to 6 and Comparative Examples 4 to 6.

The present invention provides a self-neutralizing amino acid-based cationic composition that can be dissolved or dispersed in water to provide an aqueous composition having a desirable pH value (about 3.5 to about 7) eliminating the need for pH adjustment via addition of base. The present invention also provides methods for preparing self-neutralizing amino acid-based cationic compositions and methods for preparing compositions comprising self-neutralizing amino acid-based cationic compositions.

The self-neutralizing amino acid-based cationic compositions as described herein include an amino acid-based cationic ester, i.e., a neutralized amino acid ester, a nonionic amphiphile and an anhydrous buffering agent (hereinafter "ABA"). Each component may be independently present in the composition in singular form (e.g., one type of amino acid-based cationic) or as a mixture (e.g., a mixture of two or more amino acid-based cationic esters). Details of the individual components of the composition are provided below. When dispersed or dissolved in an aqueous solvent such as water, the resultant solution/dispersion has a pH of greater than about 3.5, about 3.5 to about 7, about 4 to about 6.5, about 4 to about 5.5, or about 4 to about 5.

For use in the self-neutralizing AABC composition as described herein, one may use the neutralized amino acid ester (i.e., the amino acid-based cationic ester) (hereinafter "AABC") as described in Burgo. The contents of Burgo are imported herein by reference, and which is provided for convenience at Appendix A. In general, such AABC may be prepared from the esterification of (i) an amino acid having a non-polar side chain wherein the amine group of the amino acid has been neutralized with an acid; with (ii) a long chain fatty alcohol. The AABC may represented by the structure of formula (I):

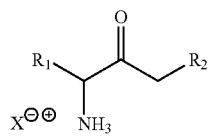

In (I), $R^1$ represents an alkyl group, which may be branched or linear. It may have one to ten carbon atoms or two to six carbon atoms. $R^2$ represents a carbon chain that may be linear or branched. It may contain ten to fifty carbon atoms or twenty-four to thirty-two carbon atoms. The chain of $R^2$ may contain at least one unsaturated carbon atom. In an embodiment, $R^2$ is an alkyl group having eight to twenty-four carbon atoms. $X^-$ represents the conjugate base of the acid used to neutralize the amino acids ester.

Amino acids for the formation of the AABC include any that are neutral. In an embodiment, one may select L-alanine, L-valine, L-leucine and L-isoleucine. Particularly preferred, in some embodiments of the invention, are L-isoleucine and L-valine. Other options may include any α,ω-aminoalkylcarboxylic acid, e.g., 11-aminoundecanoic acid or 12-aminododecanoic acid.

To obtain the ester of the invention, the amine group of the amino acid is neutralized with an acid and is reacted with a long chain fatty alcohol. Suitable fatty alcohols may be linear and/or branched and may additionally be saturated and/or unsaturated. It may be preferred that the fatty alcohol contains about ten to about fifty or about twenty-four to about thirty-two carbon atoms. In an embodiment, linear and/or branched fatty alcohols containing from about twelve to about twenty-two carbon atoms may be preferred. In another embodiment, linear fatty alcohols containing about sixteen to about twenty-four carbon atoms are preferred.

Examples of suitable fatty alcohols include lauryl alcohol, myristyl alcohol, palmityl alcohol, stearyl alcohol, oleyl alcohol, isostearyl alcohol, arachidyl alcohol, behenyl alcohol and mixtures or combinations thereof. It is advisable that the fatty alcohols are derived from non-petrochemical sources. In an embodiment, the AABC is a reaction product of the amino acid and the fatty alcohol, where the amino acid is L-alanine, L-valine, L-leucine, L-isoleucine, and/or mixtures of the same, and the fatty acid is coconut oil (including mixture of various long chain fatty acids), stearyl alcohol, isostearyl alcohol, and/or brassicyl alcohol (optionally hydrogenated). Brassica alcohol, as used herein, is defined as the fatty alcohol produced from the seed oils derived from plants of the family Brassicaceae containing or primarily containing $C_{18}$, $C_{20}$, and $C_{22}$ fatty alcohols.

In some embodiments it may be preferred that AABC a fatty alcohol ester with the amino acid being L-valine or L-isoleucine, neutralized with ethanesulfonic acid and which is preferably solid at 25° C. Such AABCs may include, for example, brassicyl valinate esylate, cetyl valinate esylate, cetearyl valinate esylate, stearyl valinate esylate, isostearyl valinate esylate, behenyl valinate esylate, octyldodecyl valinate esylate, decyltetradecyl valinate esylate; brassicyl isoleucinate esylate, cetyl isoleucinate esylate, cetearyl isoleucinate esylate, stearyl isoleucinate esylate, isostearyl isoleucinate esylate, behenyl isoleucinate esylate, octyldodecyl isoleucinate esylate, decyltetradecyl isoleucinate esylate; most preferably brassicyl valinate esylate and/or brassicyl isoleucinate esylate.

AABC may be synthesized by any methods known or developed in the art. However, illustrative examples of synthesis are provided in Burgo and are incorporated herein by this reference.

The composition also includes at least one nonionic amphiphile; it may be preferred that the selected nonionic amphiphile is one that is a solid 25° C. It may, in some embodiments, contain about 10 to about 35 carbon atoms, about 15 to about 30 carbon atoms and about 16 to about 24 carbon atoms. Exemplary nonionic amphiphiles may include:

Fatty alcohols, such as, for example, straight chain or branched fatty alcohol comprising 12 or more carbon atoms, including, for example, lauryl, myristyl, cetyl, cetearyl, stearyl, isostearyl, oleyl, arachidyl, behenyl, octyldodecyl, decyltetradecyl, coconut alcohol, palm alcohol, palm kernel alcohol, brassica alcohol, hydrogenated rapeseed alcohol; preferably linear fatty alcohol comprising 16 or more carbon atoms; most preferably brassica, cetyl, cetearyl, stearyl, or behenyl;

Fatty glyceryl esters, such as, for example, mono-, di-, or triester of glycerol or mixtures thereof that include esters of glycerol and one or more fatty acids comprising 12 or more carbon atoms, such as, for example, glyceryl laurate, glyceryl myristate, glyceryl palmate, glyceryl sesquistearate, glyceryl stearate, glyceryl stearate se, glyceryl behenate, glyceryl distearate, brassica glycerides, hydrogenated rapeseed glycerides, hydrogenated coco-glycerides, hydrogenated $C_{12-18}$ glycerides, hydrogenated palm glycerides, hydrogenated soy glycerides; preferably brassica glycerides;

Fatty glycol esters, such as, for example, mono- or diester of ethylene glycol or mixtures thereof; esters of ethylene glycol and one or more fatty acids comprising 12 or more carbon atoms, such as, glycol stearate, glycol distearate, glycol behenate, glycol dibehenate;

Fatty esters of polyglycerol, such as, for example, polyglyceryl esters are monoacyl or polyacyl esters (e.g., bearing an average of 1.5 to 10 ester groups per polyglyceryl chain) of polyglycerols having an average degree of polymerization of 2 to 10 glyceryl repeat units and having an acyl group of about 12 to about 24 carbon atoms, where acyl groups may include lauroyl, cocoyl, myristoyl, palmitoyl, stearoyl, arachidonoyl, behenoyl, and brassicoyl, such as, for example, polyglyceryl-3 stearate, polyglyceryl-3 stearate SE, polyglyceryl-4 stearate, polyglyceryl-10 stearate, polyglyceryl-6 sesquistearate, polyglyceryl-4 pentastearate, polyglyceryl-6 pentastearate, polyglyceryl-10 pentastearate polygyceryl-3 behenate, polyglyceryl-5 tribehenate, polyglyceryl-6 tetrabehenate, polyglyceryl-2 distearate, polyglyceryl-3 distearate, polyglyceryl-6 distearate, polyglyceryl-10 distearate, polyglyceryl-2 palmitate, polyglyceryl-3 palmitate, polyglyceryl-4 palmitate, polyglyceryl-6 palmitate, polyglyceryl-6 dipalmitate, polyglyceryl-4 laurate, polyglyceryl-5 laurate, polyglyceryl-6 laurate, polyglyceryl-7 laurate, polyglyceryl-8 laurate, polyglyceryl-10 laurate, polyglyceryl-2 myristate, polyglyceryl-3 myristate, polyglyceryl-4 myristate, polyglyceryl-5 myristate, polyglyceryl-6 myristate, polyglyceryl-10 myristate, and polyglyceryl-5 pentamyristate;

Fatty esters of methyl glucose such as, for example, methyl glucose esters like monoacyl or polyacyl esters (e.g., bearing an average of 1.5 to 3 ester groups per methyl glucose unit) of methyl glucose when an acyl group of about 12 to about 24 carbon atoms, where the acyl groups may include lauroyl, cocoyl, myristoyl, palmitoyl, stearoyl, arachidonoyl, behenoyl, and brassicoyl, such as, for example, methyl glucose dioleate, methyl glucose isostearate, methyl glucose laurate, methyl glucose sesquicaprylate/sesquicaprate, methyl glucose sesquicocoate, methyl glucose sesquiisostearate, methyl glucose sesquilaurate, methyl glucose sesquioleate, and methyl glucose sesquistearate;

Fatty esters of sorbitan, such as, for example, monoacyl or polyacyl esters (e.g., bearing an average of 1.5 to 4 ester groups per methyl glucose unit) of sorbitan and having an acyl group of about 12 to about 24 carbon atoms, including, for example, lauroyl, cocoyl, myristoyl, palmitoyl, stearoyl, arachidonoyl, behenoyl, and brassicoyl Examples include sorbitan cocoate, sorbitan dioleate, sorbitan distearate, sorbitan laurate, sorbitan oleate, sorbitan olivate, sorbitan palmitate, sorbitan palmate, sorbitan sesquioleate, sorbtian sesquisteatate, sorbitan stearate, sorbitan trioleate, and sorbitan tristearate.

The composition further includes an anhydrous buffering agent ("ABA"). By describing a material herein, such as the buffering agent, as "anhydrous" it is meant that the material is substantially free of added water, preferably containing less than about 5% water, more preferably less than about 4% water, even more preferably less than about 2% water, and most preferably less than about 1.5% water. Anhydrous materials may contain minor amounts of incidental water, e.g., from absorption of ambient humidity or processing conditions, e.g., washing followed by incomplete drying). In some embodiments, it is preferred that the ABA is in a particulate form or a powder form, for example, it is a finely divided solid having a small particle size, preferably less than about 100 μm.

ABAs suitable for use in the inventive composition include any known or to be developed in the art or combinations of the same. In various embodiments, the ABA is a material capable of maintaining the pH of the aqueous solution when the AABC composition is dissolved in water.

If in a powder form, the ABA may be a free-flowing solid with average particle size of less than about 100 μm, preferably less than about 75 μm, more preferably less than about 50 μm, even more preferably less than about 25 μm, in certain embodiments, the average particle size will be less than about 20 μm. In many embodiments, a powder form of small particle size may be used to facilitate the maintenance of uniform dispersion of the ABA throughout the composition during processing in the molten state and during the process of cooling and solidification to yield a solid form with buffering agent dispersed homogeneously throughout.

In various embodiments, the ABA selected may be a salt of a strong base and a weak organic acid, e.g., where strong base is sodium hydroxide, potassium hydroxide, calcium hydroxide and the like, and the weak acid is gluconic acid, citric acid, lactic acid, and the like.

Exemplary ABAs for use in the composition of the invention include, for example, alkali metals or alkaline earth metal salts of gluconic acid, e.g., sodium gluconate, calcium gluconate.

As prepared, the composition of the invention may contain any of the two/three above-described components in any relative quantity; such relative quantities may vary depending on several factors, including, for example, manufacturing parameters, the contemplated end use of the composition, and the like as is appreciated in the art. Thus, the variation of the relative quantities is a matter of routine by a person of skill in the art.

For illustration of the invention, however, it is suggested that the AABC is present in the composition in an amount of about 10 wt % to about 70 wt %, about 12 wt % to about 60 wt %, about 15 wt % to about 55 wt %, or about 20 wt % to about 50 wt %, each with reference to the weight of the total composition.

In some embodiments, one may include the ABA in the composition in the amounts of about 2 wt % to about 25 wt %, about 4 wt % to about 20 wt %, about 6 wt % to about 15 wt %, or about 8 wt % to about 12 wt %, each with reference to the weight of the total composition.

In many embodiments, the balance of the composition may be made up of the selected nonionic amphiphile(s). If other ingredients at included in the composition of the invention, the selected nonionic amphiphile(s) may be present in amount of at least about 10 wt %, about 15 wt % to about 70 wt %, in some embodiments preferably about 20 wt % to about 40 wt %, each with reference to the total composition.

In various embodiments, regardless of the amount of nonionic amphiphile present, the ratio of AABC to ABA in the composition may be: (i) on a weight basis (wt %:wt %): about 1:2 to about 1:8, about 1:2 to about 1:6, about 1:2 to about 1:4, or about 1:2 to about 1:3; or (ii) on a molar basis: about 1:1 to about 1:5, about 1:1 to about 1:4, about 1:1 to about 1:3, or about 1:1 to about 1:2. In some embodiments, the molar ratio of AABC to anhydrous buffering agent may be 1:1 or 1:2.

The composition is, in many embodiments, in an anhydrous form, preferably an anhydrous solid form.

The self-neutralizing AABC compositions may include other ingredients. Such ingredients are preferably in a powder form and/or are also anhydrous. Examples include water-soluble polymers or gums, such as guar hydroxypropyltrimonium chloride, hydroxypropyl guar, polyquaternium-10, hydroxyethyl cellulose, hydroxypropylmethyl cellulose, starch, guar gum, *cassia* gum, and the like; chelating agents, such as tetrasodium EDTA, disodium EDTA, tetrasodium glutamate diacetate, and the like; and zwitterionic surfactants, such as cocamidopropyl betaine, cocamidopropyl hydroxysultaine, lauramidopropyl betaine, and the like.

The self-neutralizing AABC compositions may also contain other solid or semi-solid ingredients that are capable of being incorporated into the composition in the molten phase, such as, for example, plant derived triglycerides, i.e., oils and butters, and waxes and wax esters, preferably nonpetrochemically derived. Other therapeutic or cosmetic benefit agents including antioxidants, such as tocopheryl acetate or ascorbyl palmitate may also be added to the self-neutralizing AABC compositions.

The self-neutralizing AABC compositions of the invention may be prepared by any process known or developed in the art. However, for illustrative purposes, a general process of manufacture is as follows: the AABC and nonionic amphiphiles are heated until completely melted and mixed to form a homogenous molten mixture. The anhydrous buffering agent is dispersed in the molten mixture to produce a uniform dispersion of the powder in the molten mixture, preferably under shear. This dispersion is maintained under heat and shear during processing to ensure it remains homogeneous while in the molten state.

In an embodiment, care should be taken to ensure that the ABA does not settle out, e.g., via sedimentation, during processing. A homogeneous mixture may be maintained by applying constant shear, e.g., with a mechanical mixer. In larger vessels, recirculation of the contents via pumping and in-line shear mixing may be combined with mechanical mixing to maintain a homogeneous dispersion of the ABA in the molten mixture.

The molten mixture is then cooled. If desired a solid may be achieved to increase convenience of subsequent post-manufacture handling and processing, if such is desired. In some embodiments, the composition may be subject to various post manufacture processes, such as for example, flaking, pastillation, prilling, beading, extrusion and pelletizing, etc. For example, the mixture can be spread in a thin layer on a chilled surface and allowed to cool and solidify; the resulting solid sheet can be broken into small pieces (flakes) and stored for subsequent compounding into formulations. The cooling and solidification processes are preferentially configured to ensure that a uniform homogeneous distribution of buffering agent is present in the solid form, e.g., from flake to flake or pastille to pastille, and from the beginning of a run to the end of a run when conducted on large scale continuously operating equipment; therefore, cooling and solidification must occur on a time scale that is much faster than the settling rate (i.e., sedimentation velocity) of the ABA particulate in the molten mixture.

The compositions of the invention may be incorporated into many consumer and industrial end formulations, for example, formulations for personal care, home & institutional care, pharmaceutical, veterinary care, oral care, textile care, metalworking, food processing, and industrial applications.

In an embodiment of the invention, the composition is incorporated with at least one other ingredient to form a formulation such as a personal care formulation. Suitable additive ingredients include water, surfactants, emollients, humectants, conditioning agents for hair, skin or nails, chelating agents, active agents, beaching or whitening agents, additional pH adjusting agents, fragrances, colorants, exfoliating agents, antioxidants, botanical ingredients, e.g., plant extracts, mica, smectite, thickeners, pharmaceuticals, cannabinoids, oils, dyes, waxes, amino acids, nucleic acids, vitamins, hydrolyzed proteins and derivatives thereof, glycerine and derivates thereof, enzymes, anti-inflammatory and other medicaments, microbiocides, antifungals, antiseptics, antioxidants, UV absorbers, dyes and pigments, preservatives, sunscreen active agents, sweat retardants, oxidizers, pH balancing agents, glyceryl monoesters, moisturizers, peptides and derivatives thereof, anti-aging actives, hair growth promoters, anti-cellulite actives and the like acceptable for use in formulations for human use.

Such formulations may have end use as, for example without limitation, a conditioner of hair, nails, skin or textile, shampoo, hair spray, mustache/beard oils or waxes, hairstyling preparation, permanent wave liquids, hair colorant, glaze, skin lotion, face & body wash, makeup remover, cleansing lotion, emollient lotion/cream. bar soap, shaving creams, sunscreen, sunburn treatment, deodorants, moisture gel, moisture essence, UV exposure-preventing essence, shaving foam, face powder, foundation, lipstick, blush, eyeliner, wrinkle and anti-aging cream, eye shadow, eyebrow pencils, mascara, mouthwash, toothpaste, an oral care composition, a skin cleansing composition, a textile cleansing compositions, a dish cleaning composition, a hair or fur cleansing composition, a deodorant or antiperspirant, a cosmetic, a hair styling composition, a skin moisturizer, a skin conditioner, a hair conditioner and a nail conditioner.

These formulations including the self-neutralizing AABC compositions of the invention may be prepared by any process known or developed in the art. However, for illustrative purposes, a general process is as follows: A water phase is heated to a temperature above the melting temperature of the self-neutralizing AABC composition and maintained under shear (mixing). While mixing, the solid self-neutralizing AABC composition is slowly added and allowed to disperse and melt into the water phase. The formulation is mixed until the buffering agent of the AABC is dissolved and a stable, uniform pH value is obtained throughout the resulting composition. Other ingredients may be added as appropriate either before or after addition of the self-neutralizing AABC composition As alternative process is as follows: The self-neutralizing AABC composition is heated to form a liquid; the liquid is maintained under shear (mixing) to ensure homogenous distribution of the buffering agent. A water phase is heated to about the same temperature as the molten self-neutralizing AABC composition. The molten self-neutralizing AABC composition is combined with the heated water phase while heating and mixing; proper agitation is employed to ensure uniform mixing of the two phases. The formulation is mixed until the buffering agent of the AABC is dissolved and a stable, uniform pH value is obtained throughout the resulting composition. In this process, other ingredients may be added as appropriate to either the water phase or the molten self-neutralizing AABC phase before the combination of the two phases, or to the resulting composition after the two phases have been combined.

For example, fatty alcohols, fatty acids, triglycerides, waxes, cosmetic oils, etc., may be mixed with the molten prior to combination with the water phase. Alternatively, water-soluble ingredients, such as humectants, chelating agents, viscosity increasing agents, e.g., water-soluble polymers, and the like, may be added to the water phase prior to combination with the molten self-neutralizing AABC phase.

In many embodiments, aqueous formulations prepared using the self-neutralizing AABC composition of the present invention will exhibit lamellar liquid crystalline (LC) phase behavior. Such LC phase behavior is readily characterized using techniques familiar to those skilled in the art, such as polarized light microscopy, small-angle X-ray scattering (SAXS), and cryo freeze-fracture scanning electron microscopy (cryo-SEM). Lamellar LC systems may be characterized by the spacing of the lamellar bilayer sheets, known as the D-spacing. The lamellar LC phases formed by the compositions of the present invention may have D-spacings as measured by SAXS from about 1 to about 100 nm, with certain embodiments having D-spacings from about 2 nm to about 25 nm, and preferred embodiments having D-spacings from about 3 nm to about 15 nm.

Those skilled in the art will recognize that the D-spacing of the lamellar LC phases can be modulated by altering one or more variables, including the carbon chain lengths of the AABCs and/or the nonionic amphiles in the self-neutralizing AABC composition, the levels of AABC and nonionic amphiles in the formulation, or the ratio of AABC to nonionic amphile(s) in either the self-neutralizing AABC composition or in the formulation itself, e.g., additional AABC or nonionic amphile may be be added to the formulation comprising the self-neutralizing AABC composition to affect the D-spacing of the lamellar LC phase. The pH, ionic strength, or level of dispersed oil phase in the formulation may also be varied to influence lamellar D-spacing. The lamellar LC phases of the present invention preferably have D-spacings that remain constant over the temperature range of 20-60° C.

In another illustrative embodiment of a method of preparing a formulation in solid format that contains the self-neutralizing compositions of the invention, the self-neutralizing AABC is heated to a molten state and mixed with appropriate agitation to maintain uniform distribution of the buffering agent in the mixture. Additional ingredients are added and mixed into the molten mixture. The mixture is cooled to yield a solid formulation that exhibits a preselected pH value upon use by the end consumer.

For example, a 10% solution of the solid formulation will preferably have a pH value of about 3.5-about 6.5, more preferably about 3.7-about 6.0, even more preferably about 3.8-about 5.5, and most preferably about 3.8-about 5.0. The solid formulation may be further processed via milling, extrusion, or other processes to incorporate additional ingredients such as surfactants, conditioning agents, fragrances, colors, exfoliating agents, or other cosmetic or therapeutic benefit agents. The solid formulation may be fabricated into a variety of forms such as bars, balls, sticks, and the like, by melting, casting into molds and allowing to solidify, or via extrusion and stamping with a press into a molded shape.

EXAMPLES

Examples 1 to 3 and Comparative Examples 1 to 3

The relative amounts of each ingredient used in Examples 1 to 3 and Comparative Examples 1 to 3 are shown below in Table 1:

TABLE 1

| | Formula Wt % (as supplied) | | | | | |
|---|---|---|---|---|---|---|
| INCI Name | Example 1 | Comp Example 1 | Example 2 | Comp Example 2 | Example 3 | Comp Example 3 |
| Brassicyl Valinate Esylate* | 27.2 | 27.2 | — | — | 31.4 | 31.4 |
| Brassicyl Isoleucinate Esylate (Brassica Alcohol)** | — | — | 36.0 | 36.0 | — | — |
| Brassica Alcohol*** | 63.3 | 72.8 | 54.4 | 64.0 | 28.8 | 34.3 |
| Brassica Glycerides | — | — | — | — | 28.8 | 34.3 |
| Calcium Gluconate (anhydrous)^ | 9.5 | — | 9.6 | — | 11.0 | — |
| Total | 100.0 | 100.0 | 100.0 | 100.0 | 100.0 | 100.0 |

*Obtained from INOLEX, Inc., as AminoSensyl AS94
**Obtained from INOLEX, Inc. as Emulsense
***Obtained from INOLEX, Inc. as SustOleo BA
****Obtained from INOLEX, Inc. as SustOleo BG
^Obtained from Spectrum Chemical Products, New Brunswick, New Jersey.

Example 1—Procedure to Prepare a Self-Neutralizing AABC Composition Using Brassicyl Valinate Esylate Brassicyl valinate esylate (BVE) and *brassica* alcohol (BA) were charged to an appropriately sized beaker equipped with overhead mechanical stirrer and propeller blade and hotplate for heating. The mixture was gently heated while manually stirring with spatula to melt the solid ingredients; upon liquefication, mixing at medium-high speed was started and the temperature brought to 75-80° C. Anhydrous calcium gluconate (CaG) powder having a D50 average particle size of 11 μm was slowly sifted into the molten BVE/BA blend and mixed until uniformly dispersed. Immediately upon stopping stirring, the mixture was poured onto a stainless steel tray, spread into a uniform thin layer, and allowed to cool to ambient temperature and solidify.

The solidified layer was scrapped off the tray to yield the flakes of the self-neutralizing AABC composition.

Comparative Example 1

The amounts in Table 1 and the procedure of Example 1 were used to prepare a comparative AABC composition. However, the calcium gluconate was omitted from the composition in this example. Note that when the ABA is omitted from the AABC composition, additional nonionic amphiphile is added in q.s. in the example to achieve 100 wt %.

Example 2—Procedure to Prepare Self-Neutralizing AABC Composition Using Brassicyl Isoleucinate Esylate The amounts in Table 1 and the procedure of Example 1 were used to prepare an AABC composition. However, in Example 2, the ABC was brassicyl isoleucinate esylate.

Comparative Example 2

The amounts in Table 1 and the procedure of Example 1 were used to prepare a comparative AABC composition. However, the calcium gluconate was omitted from the composition in this example.

Example 3—Procedure to Prepare a Self-Neutralizing AABC Composition with a Secondary Nonionic Amphiphile The amounts in Table 1 and the procedure of Example 1 were used to prepare a self-neutralizing AABC composition. However, in Example 3, the AABC was brassicyl valinate esylate and a secondary nonionic amphiphile, *brassica* glyceride, was added to the composition.

Comparative Example 3

The amounts in Table 1 and procedure of Example 1 were used to prepare a comparative AABC composition. However, the calcium gluconate was omitted from the composition in this example.

Examples 4 to 6 and Comparative Examples 4 to 6

The relative amounts of each ingredient used in Examples 4 to 6 and Comparative Examples 4 to are the same as those used in Examples 1 to 3 and Comparative Examples 1 to 3 (see Table 1). The pH data collected for each are shown below in Table 2:

TABLE 2

| Wt % AABC Composition | Example 4 (Using Example 1) | Comp Example 4 (using Comp Example 1) | Example 5 (using Example 2) | Comp Example 5 (using Comp Example 2) | Example 6 (using Example 3) | Comp Example 6 (using Comp Example 3) |
|---|---|---|---|---|---|---|
| | pH value | | | | | |
| 5 | 4.25 | 3.02 | 4.37 | 3.12 | 4.01 | 2.76 |
| 10 | 4.33 | 2.85 | 4.46 | 3.01 | 4.12 | 2.57 |
| 15 | 4.36 | 2.68 | 4.43 | 2.9 | 4.23 | 2.42 |
| 20 | 4.27 | 2.55 | 4.35 | 2.77 | 4.22 | 2.32 |

Example 4—Preparation of a Formulation Including Self-Neutralizing AABC Composition A formulation was prepared as follows: To a beaker equipped with overhead mechanical stirrer and propeller blade and hotplate for heating was charged deionized water (q.s. to 100 wt %), which was heated to 75-80° C. The Aself-neutralizing ABC composition of Example 1 in the specified amount (shown in Table 2) was slowly added to the hot water phase while mixing at medium speed and mixed until completely and uniformly dispersed. The mixture was allowed to cool to ambient temperature while mixing as low-medium speed and was then discharged to a container for storage. The formulation was allowed to equilibrate overnight and then the pH was measured using a pH meter. The compositions of Examples 4 to 6 including the self-neutralizing AABC composition were characterized using polarized light microscopy and observed to exhibit lamellar LC phase behavior, as evidenced by the characteristic Maltese cross pattern.

Figure 2:
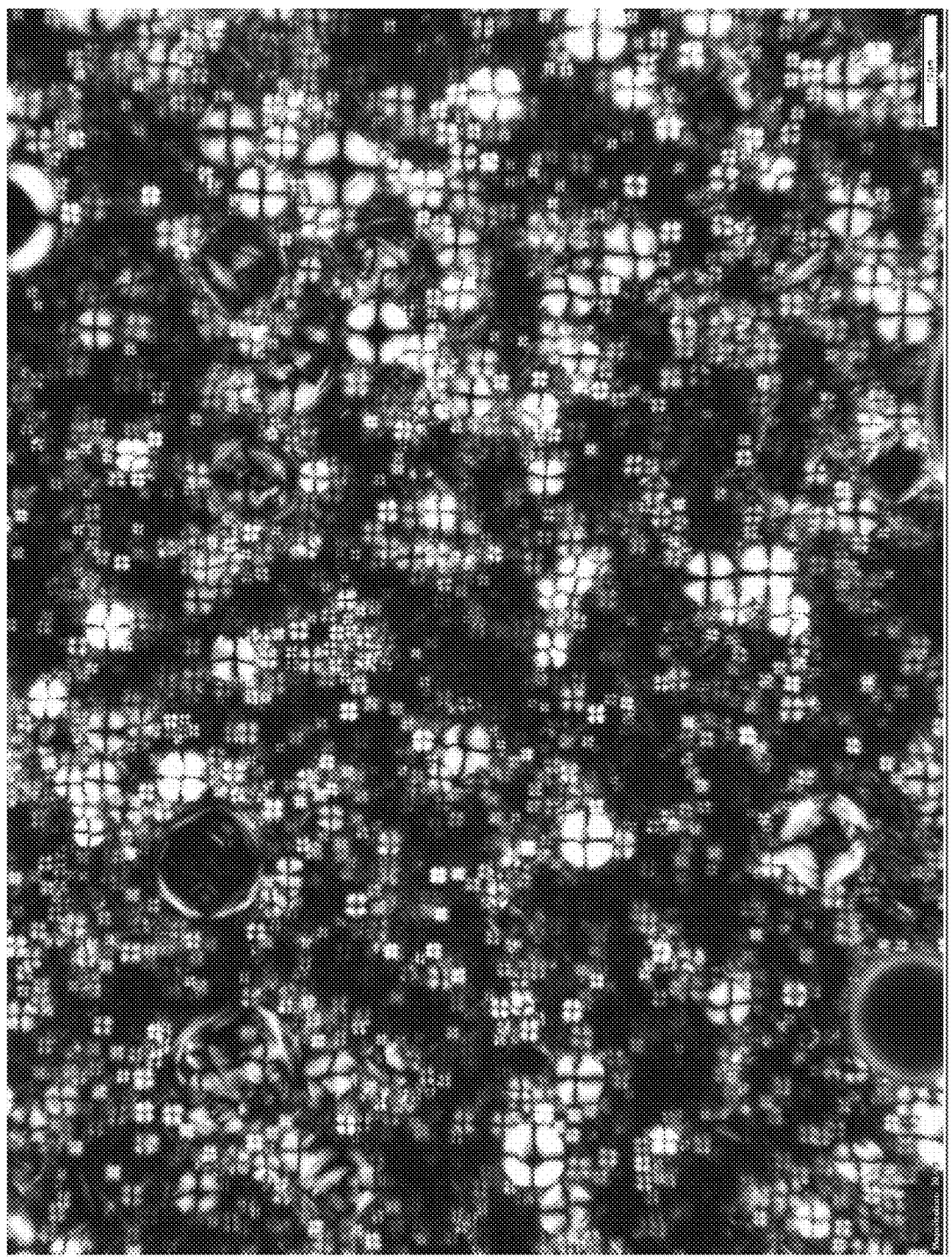
FIG. 2 is a polarized light micrograph (400× magnification) of an exemplary formulation of the invention that includes 15% of the self-neutralizing AABC composition prepared in accordance with the invention.

FIG. 2 is a polarized light micrograph (400× magnification) of the Example 4 formulation comprising 15% of the self-neutralizing AABC composition of Example 1.

The compositions of Examples 4 and 5 comprising 15% of the self-neutralizing AABC composition were analyzed via SAXS to characterize the D-spacings of the resulting lamellar LC systems over the temperature range of 20-70° C. FIGS. 3 and 4 show SAXS data for lamellar LC systems comprising brassicyl valinate esylate and brassicyl isoleucinate esylate, respectively. The peaks observed are indicative of D-spacings of 75 Å (7.5 nm) and 77 Å (7.7 nm) for the respective formulations. Disappearance of the peaks at temperatures exceeding 60° C. is indicative of a phase change to a nonlamellar system.

Comparative Example 4

The process of Example 3 was repeated using the material prepared in Comparative Example 1 in the amount specified in Table 2.

Example 5—Preparation of a Formulation Including the Self-Neutralizing AABC Composition The process of Example 4 was repeated using the self-neutralizing AABC composition prepared in Example 2 in the amount specified in Table 2.

Comparative Example 5

The process of Example 4 was repeated using the material prepared in Comparative Example 2 in the amount specified in Table 2.

Example 6—Preparation of a Formulation Including a Self-Neutralizing AABC Composition The process of Example 4 was repeated using the self-neutralizing AABC composition prepared in Example 3 in the amount specified in Table 2.

Comparative Example 6

The process of Example 4 was repeated using the material prepared in Comparative Example 3 in the amount specified in Table 2.

The pH data collected from these examples is shown in FIG. 1. The data of Table 2 and FIG. 1 demonstrate the pH buffering benefits of the self-neutralizing AABC compositions (Examples 1 to 3) when dispersed in water.

As can be seen, aqueous compositions comprising Examples 1, 2, and/or 3 demonstrate nearly constant pH values of 4.3-4.5 at concentrations ranging from 5 wt % to 20 wt % of AABC blend, whereas the comparative examples without the buffering agent (Comparative Examples 1, 2, and 3) exhibit lower pH values which decrease as a function of increasing AABC blend concentration.

Thus, the self-neutralizing AABC compositions of Examples 1, 2, and 3 provide the benefit of a pH value appropriate for the formulation of composition for hair care and skin care that is independent of use level and does not require further adjustment upon compounding in aqueous media.

Example 7—Natural Rinse-Off Hair Conditioner

Table 3 shows the relative amounts of ingredients used in the following exemplary formulation of a hair conditioner.

TABLE 3

| Ingredient (INCI) | Trade Name (Supplier) | Formula Wt % (as supplied) |
|---|---|---|
| Water | Purified Water | 84.53 |
| Caprylhydroxamic Acid (and) Propanediol | Zeastat (INOLEX) | 2.00 |
| Brassica Alcohol (and) Brassicyl Valinate Esylate (and) Calcium Gluconate | Example 1 (INOLEX) | 10.22 |
| Brassica Alcohol | SustOleo BA (INOLEX) | 0.75 |
| Triheptanoin | SustOleo MCT (INOLEX) | 1.50 |
| Diheptyl Succinate (and) Capryloyl Glycerin/ Sebacic Acid Copolymer | LexFeel N350 (INOLEX) | 0.75 |
| Argania Spinosa (Argan) Kernel Oil | Argan Oil | 0.25 |
| | | 100.00 |

To an appropriately sized beaker equipped with overhead mechanical stirrer and propeller blade and hotplate for heating was charged water and caprylhydroxamic acid (and) propanediol, which was heated to 75-80° C. while mixing at low-medium speed. At 70-75° C., the self-neutralizing AABC blend of Example 1, brassica alcohol, triheptanoin, diheptyl succinate (and) capryloyl glycerin sebacic acid copolymer, and Argania spinosa (argan) kernel oil were charged to the beaker.

The temperature was brought to 80-85° C. and the mixture was stirred for 10-15 minutes at medium-high speed. Heating was stopped and the mixture was allowed to cool to 70° C. while stirring at medium-high speed. At 70° C., the mixture was homogenized for three minutes at high speed, and then allowed to cool to 45 to 50° C. while stirring at slow speed with an anchor-type blade. At 50° C. the mixture was discharged to an appropriate container for storage. The pH of the resulting formulation was 4.20 and the Brookfield viscosity (RVT (D), helipath spindle T-C, 10 rpm) was 53,500 cP at room temperature (about 21° C.).

Example 8—Natural Leave-in Split End Mender

Table 4 shows the relative amounts of ingredients used in the following exemplary formulation of a hair spilt end mender.

TABLE 4

| Ingredient (INCI) | Trade Name (Supplier) | Formula Wt % (as supplied) |
|---|---|---|
| Oil Phase | | |
| Cetyl Alcohol | Cetyl Alcohol, NF | 5.00 |
| Diheptyl Succinate (and) Capryloyl Glycerin/ Sebacic Acid Copolymer | LexFeel N5 (INOLEX) | 5.00 |
| *Brassica* Alcohol (and) Brassicyl Valinate Esylate (and) Calcium Gluconate | Example 1 (INOLEX) | 12.50 |
| *Cocos Nucifera* (Coconut) Oil | Virgin Coconut Oil (Anjou) | 10.00 |
| Water Phase | | |
| Water | Purified Water | 61.50 |
| Caprylhydroxamic Acid (and) Benzyl Alcohol (and) Glycerin | Benzostat (INOLEX) | 1.00 |
| Glycerin | Glycerin, USP | 5.00 |
| | | 100.00 |

To an appropriately sized beaker equipped with overhead mechanical stirrer and propeller blade and hotplate for heating was charged water, caprylhydroxamic acid (and) benzyl alcohol (and) glycerin, and glycerin. Mixing was started at low-medium speed and the mixture was heated to 80° C. In a separate beaker, cetyl alcohol, diheptyl succinate (and) capryloyl glycerin sebacic acid copolymer, the self-neutralizing AABC composition of Example 1, and *Cocos nucifera* (coconut) oil were combined and heated to 80° C. while mixing and mixed until uniform.

The oil phase mixture was added to the water phase mixture at 80° C. while mixing at medium-high speed. The mixture was allowed to cool to 70° C. and then homogenized at high speed for three minutes. Following homogenization, the mixture was allowed to cool to 45-50° C. while stirring at slow speed with an anchor-type blade. At 45-50° C. the mixture was discharged to an appropriate container for storage.

The pH of the resulting formulation was 4.27 and the Brookfield viscosity (RVT (D), helipath spindle T-C, 10 rpm) was 69,600 cP at room temperature (about 21° C.).

Examples 9 and 10: Natural Hair Conditioner Bars

Table 5 shows the relative amounts of ingredients used in the following exemplary formulations of hair conditioner bars.

TABLE 5

| Ingredient— INCI Name | Trade Name (Supplier) | Formula Wt % (as supplied) | |
|---|---|---|---|
| | | Ex 9 | Ex 10 |
| *Brassica* Alcohol (and) Brassicyl Valinate Esylate (and) Calcium Gluconate | Example 1 (INOLEX) | 90.00 | 20.00 |
| *Cocos Nucifera* (Coconut) Oil | Virgin Coconut Oil (Anjou) | 3.00 | 2.00 |
| *Butyrospermum Parkii* (Shea) Butter | Cetiol SB45 (BASF) | 3.00 | — |
| Diheptyl Succinate (and) Capryloyl Glycerin/Sebacic Acid Copolymer | LexFeel N5 (INOLEX) | 1.00 | 2.00 |
| Cetyl Alcohol | Cetyl Alcohol, NF | — | 47.00 |
| Tapioca Starch | Organic Tapioca Natural (AGRANA) | — | 15.00 |
| Glycerin | Glycerin, USP | 1.00 | 2.00 |
| Caprylyl Glycol | Lexgard O (INOLEX) | 1.00 | 1.00 |
| Decyl Glucoside | Plantaren 2000 N UP (BASF) | — | 5.00 |
| Polyglyceryl-4 Oleate | Nikkol Tetraglyn 1-OV (Nikko) | — | 5.00 |
| Fragrance | Oil, Sea Island Cotton BBW (Lebermuth) | 1.00 | 1.00 |
| | | 100.00 | 100.00 |

Examples 9 and 10 were prepared by the "melt and pour" process known to those skilled in the art. The ingredients were charged to an appropriately sized beaker and heated to 80-85° C. while mixing at medium speed to maintain uniform dispersion of the buffering agent in the mixture. The fragrance was withheld from the mixture until the final 1-2 minutes of mixing. Following fragrance addition, the mixture was immediately discharged to cooled bar molds and cooled rapidly to maintain a uniform, homogenous solid form. The pH values of a 10% solution of the bar compositions in water were 4.09 and 5.39 for Example 9 and Example 10, respectively.

Example 11 and Comparative Example 11—Therapeutic Lotion Formulas

Table 6 shows the relative amounts of ingredients used in the formulations of therapeutic lotion formulas of Example 11 and Comparative Example 11. The elucidated viscosity and pH of each formulation are also shown in Table 6.

TABLE 6

| Ingredient— INCI Name | Trade Name (Supplier) | Formula Wt % (as supplied) | |
|---|---|---|---|
| | | Example 11 | Comp Example 10 |
| Water | Deionized Water | 70.82 | 71.74 |
| Sodium Chloride | Sodium Chloride (Morton) | 0.01 | 0.01 |
| Glycerin | Glycerin | 12.00 | 12.00 |
| Colloidal Oatmeal | AVEENO ® Oatmeal Bath (Johnson & Johnson) | 1.00 | 1.00 |

TABLE 6-continued

| Ingredient— INCI Name | Trade Name (Supplier) | Formula Wt % (as supplied) | |
|---|---|---|---|
| | | Example 11 | Comp Example 10 |
| Brassicyl Valinate Esylate (and) *Brassica* Alcohol (and) *Brassica* Glycerides (and) Calcium Gluconate | Example 3 (INOLEX) | 6.92 | — |
| Brassicyl Valinate Esylate (and) *Brassica* Alcohol (and) *Brassica* Glycerides | Comparative Example 3 (INOLEX) | — | 6.00 |
| Isopropyl Palmitate | Lexol IPP (INOLEX) | 3.00 | 3.00 |
| Petrolatum | Vaseline ® Jelly (Unilever) | 4.00 | 4.00 |
| Dimethicone | XIAMETER ™ PMX-200 Silicone Fluid 20 cSt (Dow) | 1.25 | 1.25 |
| Caprylhydroxamic Acid (and) Benzyl Alcohol (and) Glycerin | Benzostat ™ (INOLEX) | 1.00 | 1.00 |
| | TOTAL | 100.00 | 100.00 |
| | pH | 4.19 | 2.73 |
| | viscosity | 12,400 | 5,400 |

Example 11

To an appropriately sized beaker equipped with overhead mechanical stirrer and propeller blade and hotplate for heating was charged water, sodium chloride, and glycerin. Mixing was started at medium speed and heating started to bring batch temperature to 80-85° C. Colloidal oatmeal was slowly sifted into the batch and mixed until uniformly dispersed with no appearance of lumps.

When the temperature reached 60-65° C., the self-neutralizing AABC of Example 3 was added along with isopropyl palmitate, petrolatum, and dimethicone. Upon reaching 80-85° C., the batch was mixed at medium-high speed for 10-15 minutes to ensure all ingredients were melted and uniformly dispersed. Heating was stopped and the batch allowed to cool to ca. 70° C. with continued mixing. At 70° C., the batch was homogenized at 3000 rpm for three minutes and then mixing was resumed at low-medium speed while allowing to cool. Once the batch temperature cooled to 55° C., caprylhydroxamic acid (and) benzyl alcohol (and) glycerin were added. The mixture was allowed to cool to 40-45° C. while stirring at slow speed with an anchor-type blade.

At ca. 40° C., the mixture was discharged to an appropriate container for storage. The pH of the resulting formulation was 4.19 and the Brookfield viscosity (RVT (D), helipath spindle T-C, 10 rpm) was 12,400 cP at room temperature (about 21° C.).

Comparative Example 11

Comparative Example 11 was prepared using Comparative Example 3, a non self-neutralizing AABC composition, according to the same process as Example 11. The resulting lotion exhibited an undesirably low pH value (2.73) and an undesirably low viscosity (5,400 cP) compared to Example 11.

Example 12 and Comparative Example 12—High Emollient Skin Cream

Table 7 shows the relative amounts of ingredients used in the formulations Example 12 and Comparative Example 12. The elucidated viscosity and pH of each formulation are also shown in Table 7.

TABLE 7

| Ingredient— INCI Name | Trade Name (Supplier) | Formula Wt % (as supplied) | |
|---|---|---|---|
| | | Example 12 | Comp Example 12 |
| Main Batch (Water Phase) | | | |
| Water | Deionized Water | 62.48 | 64.01 |
| Caprylhydroxamic Acid (and) Glyceryl Caprylate (and) Glycerin | Spectrastat ™ G2 (INOLEX) | 1.00 | 1.00 |
| Oil Phase | | | |
| Brassicyl Valinate Esylate (and) *Brassica* Alcohol (and) *Brassica* Glycerides (and) Calcium Gluconate | Example 3 (INOLEX) | 11.53 | — |
| Brassicyl Valinate Esylate (and) *Brassica* Alcohol (and) *Brassica* Glycerides | Comparative Example 3 (INOLEX) | — | 10.00 |
| *Helianthus Annus* (Sunflower) Seed Oil | Sunflower Seed Oil | 8.33 | 8.33 |
| Caprylic/Capric Triglyceride | Lexol ™ GT-865 (INOLEX) | 8.33 | 8.33 |
| Isopropyl Palmitate | Lexol ™ IPP (INOLEX) | 8.33 | 8.33 |
| | TOTAL | 100.00 | 100.00 |
| | pH | 4.16 | 2.55 |
| | viscosity | 69,400 | 21,800 |

Example 12

In an appropriately sized beaker equipped with overhead mechanical stirrer and propeller blade and hotplate for heating, an oil phase was prepared by combining *Helianthus annus* (sunflower) seed oil, caprylic/capric triglyceride, and isopropyl palmitate. The mixture was heated to 75-80° C. while mixing at low-medium speed. While heating, the self-neutralizing AABC composition of Example 3 was added and the oil phase mixed until uniform.

The oil phase was held at 75-80° C. with mixing to maintain a uniform dispersion without sedimentation. In a separate beaker equipped with equipped with overhead mechanical stirrer and propeller blade and hotplate for heating, water and caprylhydroxamic acid (and) glyceryl caprylate (and) glycerin were combined and heated to 75-80° C. while mixing at low-medium speed. At 75-80° C., mixing speed was increased to medium-high and the hot oil phase was added to the main batch and allowed to mix at 75-80° C. until uniform.

Heating was stopped and the batch was allowed to cool to ca. 70° C. and then homogenized at 3000 rpm for three minutes. Mixing was resumed at low-medium speed with an anchor-type bladed while allowing to cool. Once the batch temperature cooled to ca. 45-50° C., the mixture was discharged to an appropriate container for storage. The pH of the resulting formulation was 4.16 and the Brookfield viscosity (RVT (D), heilapath spindle T-C, 10 rpm) was 69,400 cP at room temperature (about 21° C.).

Comparative Example 12

Comparative Examples 12 was prepared using Comparative Example 3, a nonself-neutralizing AABC composition, according to the same process as Example 12. The resulting cream exhibited an undesirably low pH value (2.55) and an undesirably low viscosity (21,800 cP) compared to Example 12.

Example 13—Natural Shave Lotion

Example 13 was prepared according to the same general procedure described in Example 12. *Citrus aurantium dulcis* (orange) peel oil and fragrance were post-added to the batch during the cooling period when the temperature had cooled to <55° C. The pH of the resulting formulation was 4.03 and the Brookfield viscosity (RVT (D), helipath spindle T-C, 10 rpm) was 50,400 cP at room temperature (about 21° C.).

Table 8 shows the ingredients and their relative amounts as used for Example 13.

TABLE 8

| Ingredient—<br>INCI Name | Trade Name<br>(Supplier) | Formula Wt %<br>(as supplied)<br>Ex 13 |
|---|---|---|
| Water Phase | | |
| Deionized Water | Deionized Water | 75.32 |
| Glycerin | Glycerin | 3.00 |
| Caprylhydroxamic Acid (and) Glyceryl Caprylate (and) Glycerin | Spectrastat ™ (INOLEX) | 1.00 |
| Oil Phase | | |
| Brassicyl Valinate Esylate (and) *Brassica* Alcohol (and) *Brassica* Glycerides (and) Calcium Gluconate | Example 3 (INOLEX) | 10.38 |
| Triheptanoin (and) C13-15 Alkane | LexFeel ™ WOW-A (INOLEX) | 4.00 |
| Diheptyl Succinate (and) Caprylyl Glycerin/Sebacic Acid Copolymer | LexFeel ™ N100 (INOLEX) | 4.00 |
| *Simmondsia Chinensis* (Jojoba) Seed Oil | Jojoba Oil (Now Solutions) | 2.00 |
| Post Adds | | |
| *Citrus Aurantium Dulcis* (Orange) Peel Oil | Orange Peel Oil (Now Solutions) | 0.15 |
| Fragrance | Oil, Euc/Spearmint BBW Type (Lebermuth Co.) | 0.15 |
| | TOTAL | 100.00 |

Where applicable, chemicals are specified by their INCI Name according to the guidelines of the International Nomenclature of Cosmetic Ingredients. Additional information, including suppliers and trade names, can be found under the appropriate INCI monograph in the International Cosmetic Ingredient Dictionary and Handbook, 16th Edition published by the Personal Care Products Council, Washington, D.C., or online in the Personal Care Products Council On-Line INFOBASE (http://online.personalcarecouncil.org).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A self-neutralizing amino acid-based cationic composition comprising an amino acid-based cationic ester in an amount of about 10 wt % to about 70 wt %, an anhydrous buffering agent in an amount of about 2 wt % to about 25 wt %, and a nonionic amphiphile in an amount sufficient to total 100 wt % of the composition,
   wherein the amino acid-based cationic ester is selected from brassicyl valinate esylate, cetyl valinate esylate, cetearyl valinate esylate, stearyl valinate esylate, isostearyl valinate esylate, behenyl valinate esylate, octyldodecyl valinate esylate, decyltetradecyl valinate esylate; brassicyl isoleucinate esylate, cetyl isoleucinate esylate, cetearyl isoleucinate esylate, stearyl isoleucinate esylate, isostearyl isoleucinate esylate, behenyl isoleucinate esylate, octyldodecyl isoleucinate esylate, decyltetradecyl isoleucinate esylate, and mixtures thereof, wherein the anhydrous buffering agent is selected from sodium gluconate, potassium gluconate, calcium gluconate, sodium citrate, potassium citrate, calcium citrate, sodium lactate, potassium lactate, calcium lactate, and mixtures thereof; and
   wherein the composition is in anhydrous solid form.

2. The composition of claim 1, wherein the nonionic amphiphile is selected from a fatty alcohol, a fatty glyceryl ester, fatty glycol esters, fatty esters of polyglycerol, fatty esters of methyl glucose, fatty esters of sorbitan and mixtures thereof.

3. The composition of claim 2, wherein the nonionic amphiphile has about 10 to about 35 carbon atoms.

4. The composition of claim 1, wherein the nonionic amphiphile is *brassica* alcohol and the amino acid-based cationic ester is selected from brassicyl valinate esylate and brassicyl isoleucinate esylate.

5. An aqueous formulation comprising the self-neutralizing amino acid-based cationic composition of claim 1, water, and at least one additive, and having a pH greater than 4.

6. The aqueous formulation of claim 5 wherein the at least one additive is selected from emollients, humectants, conditioning agents, chelating agents, pH adjusting agents, fragrance, colorant, exfoliating agents, antioxidants, silica, plant extracts, surfactants, and mixtures thereof.

7. The composition of claim 1, wherein the composition is in the form of a solid bar.

8. The composition of claim 7, wherein a 10% solution of the solid bar has a pH greater than 4.

9. The composition of claim 7, wherein a 10% solution of the solid bar has a pH greater than 5.

10. The composition of claim 1, wherein the amino acid-based cationic ester includes two or more amino acid-based cationic esters selected from brassicyl valinate esylate, cetyl valinate esylate, cetearyl valinate esylate, stearyl valinate esylate, isostearyl valinate esylate, behenyl valinate esylate, octyldodecyl valinate esylate, decyltetradecyl valinate esylate; brassicyl isoleucinate esylate, cetyl isoleucinate esylate, cetearyl isoleucinate esylate, stearyl isoleucinate esylate, isostearyl isoleucinate esylate, behenyl isoleucinate esylate, octyldodecyl isoleucinate esylate, decyltetradecyl isoleucinate esylate, and mixtures thereof.

11. The composition of claim 1, wherein the nonionic amphiphile includes two or more nonionic amphiphiles selected from a fatty alcohol, a fatty glyceryl ester, fatty glycol esters, fatty esters of polyglycerol, fatty esters of methyl glucose, fatty esters of sorbitan and mixtures thereof.

12. A self-neutralizing amino acid-based cationic composition comprising:
about 10 wt % to about 70 wt % an amino acid-based cationic ester;
about 2 wt % to about 25 wt % an anhydrous buffering agent; and
a nonionic amphiphile in an amount sufficient to total 100 wt % of the composition;
wherein the amino acid-based cationic ester is selected from brassicyl valinate esylate, cetyl valinate esylate, cetearyl valinate esylate, stearyl valinate esylate, isostearyl valinate esylate, behenyl valinate esylate, octyldodecyl valinate esylate, decyltetradecyl valinate esylate; brassicyl isoleucinate esylate, cetyl isoleucinate esylate, cetearyl isoleucinate esylate, stearyl isoleucinate esylate, isostearyl isoleucinate esylate, behenyl isoleucinate esylate, octyldodecyl isoleucinate esylate, decyltetradecyl isoleucinate esylate, and mixtures thereof, and
wherein the anhydrous buffering agent is selected from an alkali metal or alkaline earth metal salt of gluconic acid and mixtures thereof.

13. The composition of claim 12, further comprising water and having a pH greater than 3.5.

14. The composition of claim 12, further comprising water and having a pH greater than 4.

15. The composition of claim 1, wherein the amino acid-based cationic ester is brassicyl valinate esylate and the anhydrous buffering agent is calcium gluconate.

16. The composition of claim 1, wherein the amino acid-based cationic ester is brassicyl isoleucinate esylate and the anhydrous buffering agent is calcium gluconate.

17. The composition of claim 12, wherein the amino acid-based cationic ester is brassicyl valinate esylate and the anhydrous buffering agent is calcium gluconate.

18. The composition of claim 12, wherein the amino acid-based cationic ester is brassicyl isoleucinate esylate and the anhydrous buffering agent is calcium gluconate.

* * * * *